United States Patent
Yang et al.

(10) Patent No.: US 12,097,309 B2
(45) Date of Patent: *Sep. 24, 2024

(54) AEROSOL GENERATOR INCLUDING MULTI-COMPONENT WICK

(71) Applicant: Philip Morris USA Inc., Richmond, VA (US)

(72) Inventors: Zuyin Yang, Midlothian, VA (US); Susan E. Wrenn, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 605 days.

This patent is subject to a terminal disclaimer.

(21) Appl. No.: 17/076,163

(22) Filed: Oct. 21, 2020

(65) Prior Publication Data
US 2021/0030912 A1     Feb. 4, 2021

Related U.S. Application Data

(63) Continuation of application No. 15/333,850, filed on Oct. 25, 2016, now Pat. No. 10,828,385, which is a
(Continued)

(51) Int. Cl.
*A61L 9/03*     (2006.01)
*A01M 1/20*     (2006.01)
(Continued)

(52) U.S. Cl.
CPC ........... *A61L 9/037* (2013.01); *A01M 1/2077* (2013.01); *A61L 9/035* (2013.01); *A61M 11/041* (2013.01);
(Continued)

(58) Field of Classification Search
CPC .................................. A61L 9/03; A01M 1/20
See application file for complete search history.

(56) References Cited

U.S. PATENT DOCUMENTS

| | | | |
|---|---|---|---|
| 47,173 A * | 4/1865 | Speakman | ............... F23D 3/40 |
| | | | 431/299 |
| 2,057,353 A | 10/1936 | Whittmore, Jr. | |
| | (Continued) | | |

FOREIGN PATENT DOCUMENTS

| | | |
|---|---|---|
| CN | 2688058 Y | 3/2005 |
| CN | 1700931 A | 11/2005 |
| | (Continued) | |

OTHER PUBLICATIONS

Zeus Industrial Products, "Dielectric Properties of Polymers" retrieved from https://www.appstate.edu/~clementsjs/journalarticles/zeus_dielectric.pdf on Oct. 25, 2023 (Year: 2005).*
(Continued)

*Primary Examiner* — Helena Kosanovic
*Assistant Examiner* — Lawrence H Samuels
(74) *Attorney, Agent, or Firm* — Harness, Dickey & Pierce, P.L.C.

(57) ABSTRACT

An aerosol generator includes a composite conduit to transport multiple liquids to a heating element at flow rates such that the liquids arrive at the heating element in desirable concentrations. The heating element volatilizes the liquids to form volatilized fluid, which mixes with ambient air to form an aerosol with desirable concentrations of the multiple liquids.

13 Claims, 3 Drawing Sheets

Related U.S. Application Data continuation of application No. 13/008,563, filed on Jan. 18, 2011, now Pat. No. 9,555,198, which is a continuation of application No. 12/791,407, filed on Jun. 1, 2010, now abandoned, which is a continuation of application No. 12/576,951, filed on Oct. 9, 2009, now abandoned.

(51) Int. Cl.
*A61L 9/015* (2006.01)
*A61M 11/04* (2006.01)
*A61M 15/00* (2006.01)

(52) U.S. Cl.
CPC ...... *A61M 11/042* (2014.02); *A61M 15/0003* (2014.02); *A61M 15/0021* (2014.02); *A61M 2205/8206* (2013.01)

(56) References Cited

U.S. PATENT DOCUMENTS

| | | | |
|---|---|---|---|
| 3,695,267 A | 10/1972 | Hirtz et al. | |
| 4,419,302 A | 12/1983 | Nishino et al. | |
| 4,676,237 A * | 6/1987 | Wood ............... | A61M 16/16 261/130 |
| 4,682,010 A | 7/1987 | Drapeau et al. | |
| 4,903,761 A * | 2/1990 | Cima ............... | F28D 15/043 165/41 |
| 4,922,901 A | 5/1990 | Brooks et al. | |
| 4,947,874 A | 8/1990 | Brooks et al. | |
| 5,095,921 A | 3/1992 | Losee et al. | |
| 5,179,966 A | 1/1993 | Losee et al. | |
| 5,388,594 A | 2/1995 | Counts et al. | |
| 5,647,053 A * | 7/1997 | Schroeder ......... | A01M 1/2077 392/390 |
| 5,743,251 A | 4/1998 | Howell et al. | |
| 6,249,645 B1 | 6/2001 | Smith | |
| 6,325,475 B1 * | 12/2001 | Hayes ............... | A61M 11/042 604/28 |
| 6,568,390 B2 | 5/2003 | Nichols et al. | |
| 6,666,909 B1 | 12/2003 | TeGrotenhuis et al. | |
| 6,715,487 B2 | 4/2004 | Nichols et al. | |
| 6,869,462 B2 | 3/2005 | TeGrotenhuis et al. | |
| 6,875,247 B2 | 4/2005 | TeGrotenhuis et al. | |
| 6,899,280 B2 | 5/2005 | Kotary et al. | |
| 6,950,607 B2 * | 9/2005 | Yip ............... | A61L 9/035 392/390 |
| 7,007,863 B2 * | 3/2006 | Kotary ............... | A01M 1/2077 122/366 |
| 7,055,764 B1 * | 6/2006 | Martinez ............ | A61L 9/127 239/145 |
| 7,167,641 B2 | 1/2007 | Tam et al. | |
| 7,281,670 B2 * | 10/2007 | Lakatos ............ | A61L 9/037 122/366 |
| 9,999,250 B2 | 6/2018 | Minskoff et al. | |
| 2002/0112723 A1 | 8/2002 | Schuster et al. | |
| 2002/0146242 A1 | 10/2002 | Vieira | |
| 2002/0181946 A1 | 12/2002 | Brown et al. | |
| 2003/0168520 A1 | 9/2003 | Triplett et al. | |
| 2003/0170014 A1 * | 9/2003 | Triplett ............ | A61L 9/03 392/395 |
| 2004/0035409 A1 | 2/2004 | Harwig et al. | |
| 2004/0065749 A1 * | 4/2004 | Kotary ............... | A01M 1/2072 239/44 |
| 2005/0074370 A1 * | 4/2005 | Yuan ............... | A61L 9/037 422/126 |
| 2005/0155985 A1 | 7/2005 | Meyer | |
| 2005/0175331 A1 * | 8/2005 | Tam ............... | A61L 9/037 392/405 |
| 2005/0279854 A1 | 12/2005 | Martens et al. | |
| 2006/0011733 A1 | 1/2006 | Varanasi et al. | |
| 2006/0163152 A1 | 7/2006 | Ward et al. | |
| 2006/0180143 A1 | 8/2006 | Lind et al. | |
| 2007/0217771 A1 | 9/2007 | Granger et al. | |
| 2007/0237499 A1 | 10/2007 | DeWitt et al. | |
| 2007/0262478 A1 | 11/2007 | Price et al. | |
| 2008/0017667 A1 | 1/2008 | Valinotti | |
| 2008/0092912 A1 | 4/2008 | Robinson et al. | |
| 2008/0135640 A1 | 6/2008 | Velazquez et al. | |
| 2008/0315011 A1 | 12/2008 | Pesu | |
| 2009/0020625 A1 | 1/2009 | Trevino | |
| 2009/0057437 A1 | 3/2009 | Blondeau et al. | |
| 2009/0101729 A1 * | 4/2009 | Newman ............ | A61L 9/042 210/799 |
| 2009/0194607 A1 * | 8/2009 | Nichols ............. | A61L 9/037 239/13 |
| 2010/0206306 A1 | 8/2010 | Feriani et al. | |
| 2011/0253798 A1 * | 10/2011 | Tucker ............. | A01M 1/2077 239/13 |
| 2013/0306084 A1 | 11/2013 | Flick | |
| 2016/0021930 A1 | 1/2016 | Minskoff et al. | |

FOREIGN PATENT DOCUMENTS

| | | | |
|---|---|---|---|
| CN | 200976794 Y | 11/2007 | |
| CN | 101087520 A | 12/2007 | |
| CN | 201230534 Y | 5/2009 | |
| EP | 0488488 A1 | 6/1992 | |
| EP | 0 448 488 B1 | 4/1995 | |
| GB | 2149684 A | 6/1985 | |
| GB | 2449703 A | 12/2008 | |
| GB | 2450134 A | 12/2008 | |
| JP | 05295701 A * | 11/1993 | ............ Y02A 30/30 |
| JP | H11-033097 A | 2/1999 | |
| UA | 36768 U | 11/2008 | |
| WO | WO-2004032983 A1 | 4/2004 | |
| WO | WO-2006004902 A1 | 1/2006 | |
| WO | WO-2006086904 A1 | 8/2006 | |

OTHER PUBLICATIONS

Notice of Allowance dated Dec. 9, 2014 for Ukrainian Patent Appln. No. 201205053.
Japanese Official Action issued Aug. 4, 2014 for Japanese Appln. No. 2012-532499.
International Preliminary Report on Patentability mailed Apr. 11, 2012 for PCT/EP2010/006198.
International Search Report and Written Opinion mailed Dec. 20, 2010 for International Application No. PCT/EP2010/006198.
Office Action for corresponding Canadian Application No. 2,941,727 dated Oct. 14, 2016.
European Office Action issued Jun. 28, 2016 in corresponding European Patent Application No. 10774131.6 (5 pages).
Utada et al., "Monodisperse Double Emulsions Generated From a Mircocapillary Device", www.sciencemag.org, Science, vol. 308, Apr. 22, 2005, pp. 537-541.
Notice of Allowance dated Dec. 9, 2014 for Ukrainian Patent Application No. 201205053.
Japanese Office Action issued Aug. 4, 2014 for Japanese Application No. 2012-532499.
Indonesian Office Action for corrresponding Application No. P00201606265 dated Jan. 11, 2019, English translation thereof.
Chinese Office Action for corrresponding Application No. 201610801200.6 dated Dec. 19, 2018.
Indian Office Action for corresponding Application No. 2856/DELNP/2012, dated Feb. 18, 2019.
Australian Office Action for corresponding Application No. 2018201565, dated Sep. 7, 2018.
European Notice of Allowance for corresponding Application No. 16183643.2-1122, dated Feb. 7, 2020.
Vietnamese Notice of Opposition for corresponding Application No. 1-2012-01154, dated Oct. 4, 2017.
Vietnamese Notice of Opposition for corresponding Application No. 1-2016-03257, dated Oct. 2, 2017.

(56) References Cited

OTHER PUBLICATIONS

Chinese Office Action dated Jul. 9, 2021 for corresponding Chinese Application No. 201610801200.6, and English-language translation thereof.

* cited by examiner

AEROSOL GENERATOR INCLUDING MULTI-COMPONENT WICK

CROSS REFERENCE TO RELATED APPLICATION

This application is a continuation of, and claims priority under 35 U.S.C. § 120 to, U.S. application Ser. No. 15/333,850, filed Oct. 25, 2016, which is a continuation of, and claims priority under 35 U.S.C. § 120 to, U.S. application Ser. No. 13/008,563, filed Jan. 18, 2011, which is a continuation of, and further claims priority under 35 U.S.C. § 120 to U.S. application Ser. No. 12/791,407, filed Jun. 1, 2010, which is a continuation of and further claims priority under 35 U.S.C. § 120 to U.S. application Ser. No. 12/576,951, filed Oct. 9, 2009, the entire contents of each of which are incorporated herein by reference.

SUMMARY

Provided is an aerosol generator including a composite conduit to transport multiple liquids to a heating element such that the liquids arrive at the heating element in desirable concentrations. The heating element is operable to volatilize the liquids to form volatilized fluid, which mixes with ambient air to form an aerosol with desirable concentrations of the multiple liquids.

Also provided is a method of generating an aerosol comprising transporting first and second liquids through first and second wicks from at least one liquid supply to a heating element at rates such that the liquids are present at the heating element in desirable concentrations and volatilizing the liquids at the heating element to form volatilized fluid, which mixes with ambient air to form an aerosol with desirable concentrations of the liquids.

BRIEF DESCRIPTION OF THE DRAWINGS

FIG. 1a is a side view of the arrangement and FIG. 1b is a cross-sectional view of the arrangement.

FIG. 3b shows a cross section of the composite conduit shown in FIG. 3a.

DETAILED DESCRIPTION OF PREFERRED EMBODIMENTS

Figure 1B:
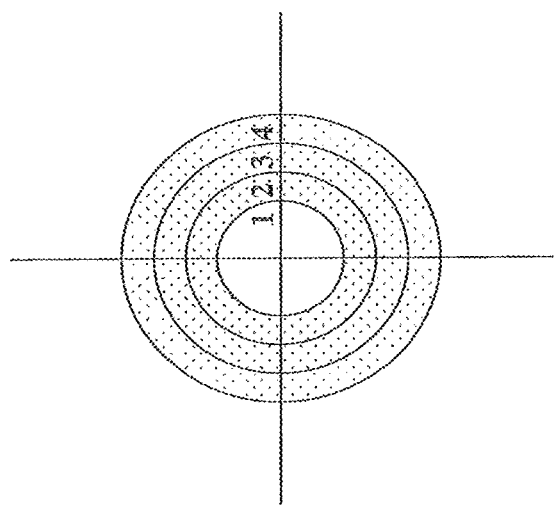
FIGS. 1a and 1b are schematics of an embodiment of an arrangement containing plural layers of wicking materials for transporting a multi phase solution. Specifically.

Provided is a device for generation of an aerosol. The device may be used for various purposes such as generating flavored aerosols, scented aerosols, or the like. The device volatilizes liquid material, which optionally condenses in ambient air to form an aerosol.

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. For aerosols intended for human inhalation, a mass median particle diameter of particles of the aerosol less than 2 microns, preferably between 0.2 and 2 microns, and more preferably between 0.5 and 1 micron, is preferred.

Aerosols and the precursor vapor may also have applications in creating nano particles and other powders. The volatilization of metal containing liquids brings the possibility of producing micro ball bearings, foam metal and metal plating in a precise and cost effective manner. The uses of aerosols and the precursor vapor also have applications in the area of lubrication, where disbursement of the lubricant may be facilitated with the introduction of a concentration of particles of lubricant.

In a preferred embodiment, the device includes a composite conduit having plural passages which transport liquids to form an aerosol. The passages can be capillary tubes, wicks, wicks of various wicking material or a combination thereof. More specifically, the composite conduit can be used to transport liquids from at least one liquid supply to a heating element at rates such that the liquids are present at the heating element in desirable concentrations. The heating element volatilizes the liquids to form volatilized fluid, which mixes with ambient air to form an aerosol with desirable concentrations of the liquids.

As used herein, "desirable concentrations" refer to concentrations that will produce an aerosol with preferred characteristics, which is dependent upon the composition of the liquids that are volatized to form the aerosol. Accordingly, the ratio and amounts of the liquids transported to the heating element determines the composition of the aerosol formed.

In a preferred embodiment, the ratio and amounts of the liquids transported to the heating element may be controlled through selection of the passages (capillary tubes, wicks, wick material) and liquids. Preferably, two or more liquids are transported and the liquids preferably are immiscible in each other. If stored together in a single liquid supply, the immiscible liquids may form multiple phases. The wicks operate by capillary action and may be combined with one or more capillary tubes. In an example, two or more wicks and a capillary tube would be adapted to transport a plurality of liquids. Preferably, wicks contain numerous pores, which act as capillaries and cause the liquid to be drawn into them. Wicks may be selected based on their wettability for an immiscible liquid or phase. The capillary tube preferably has an internal diameter of 0.1 to 10 mm, preferably 0.5 to 1 mm, more preferable about 0.1 to 0.5 mm, and even more preferably about 0.15 mm, corresponding to internal cross sectional areas of 8×10-5 to 80 $mm^2$, 0.002 to 0.8 $mm^2$, 0.008 to 0.2 $mm^2$, and about 0.02 $mm^2$, respectively. The dimensions of the capillaries and/or wicks are further factors that affect the amounts of liquids transported to the heating element.

Various geometries can be used for transporting the liquids at desired flow rates to the heating element. For example, multiple wicking materials, such as, for example, one or more synthetic fibers and cotton, may be combined to form a woven wick to transport one or more liquids. In an embodiment, wicking materials may be arranged in a concentric pattern around a central capillary tube, such as two or more tubes of wicking materials arranged in a concentric pattern around a central capillary tube. The wicking materials may be separated by wire mesh, which may also act as a wicking material for liquid transport.

Figure 1A:
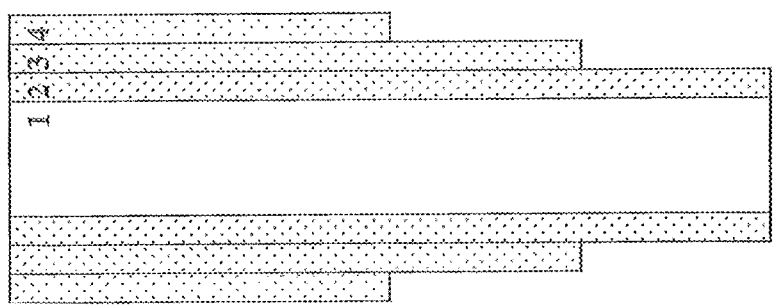

FIGS. 1a and 1b are schematics of an arrangement containing three layers of wicking materials for transporting a three phase solution. Specifically, FIG. 1a is a side view of a coaxial arrangement and FIG. 1b is a cross-sectional view of the arrangement. In particular, a capillary tube 1 is concentrically surrounded by three layers 2, 3, 4 of wicking materials. It is furthermore possible for a four phase solution to be transported, with the capillary tube 1 transporting one phase and the three layers 2, 3, 4 of wicking materials transporting three other phases. If desired, the capillary tube and/or the fourth wick can be omitted.

The immiscible liquid may comprise one or more hydrophobic liquids (e.g., one or more essential oils) and one or more hydrophilic liquids (e.g., propylene glycol, glycerol and/or other aerosol former). In a reservoir containing a multiphase liquid, the phases may separate into discrete layers with lower density phases forming over higher density phases. An arrangement for transporting immiscible liquids may comprise passages having different lengths adapted to be in contact with different layers of the multiphase liquid. In the case of a two phase immiscible liquid comprising a lighter flavor-rich phase and a heavier aerosol former phase, first and second wicks or capillary tubes for transporting the immiscible liquids may comprise a shorter wick or shorter capillary tube adapted to be in contact with the lighter flavor-rich liquid and a longer wick or longer capillary tube adapted to be in contact with the heavier aerosol former. Further, if the first and second wicks/capillary tubes for transporting the immiscible liquids are arranged in a concentric pattern, the shorter wick/capillary tube adapted to be in contact with the lighter flavor-rich liquid may surround the longer wick/capillary tube adapted to be in contact with the heavier aerosol former.

Thus, an aerosol generator can comprise an arrangement for transporting immiscible liquids from at least one liquid supply to a heating element at rates such that the liquids are present at the heating element in desirable concentrations. The heating element volatilizes the immiscible liquids to form volatilized fluid, which mixes with ambient air to form an aerosol with desirable concentrations of the immiscible liquids.

The heating element may comprise a wire mesh heater embedded in a downstream end of the wicks. The heating element may be a stainless steel wire mesh or a stainless steel serpentine strip. The heating element is connected to a power supply, which can be a portable power supply such as a direct current battery. However, the use of alternating current may also be effective. When the aerosol generator comprises one or more capillary tubes, the heating element is operable to volatilize the liquid(s) transported via the capillary tube(s) at the downstream end of the capillary tube(s), similar to the volatilization of the liquids transported via the wicks at the downstream end of the wicks.

The immiscible liquids preferably comprise multiple phases, which are transported from one liquid supply. However, the liquids can be supplied from different liquid supplies if desired. The immiscible liquids may comprise at least one hydrophobic liquid and at least one hydrophilic liquid such as a flavor system and aerosol former. The flavor system may comprise one or more essential oils. The aerosol former may comprise propylene glycol, glycerol, or mixtures thereof.

Figure 2:
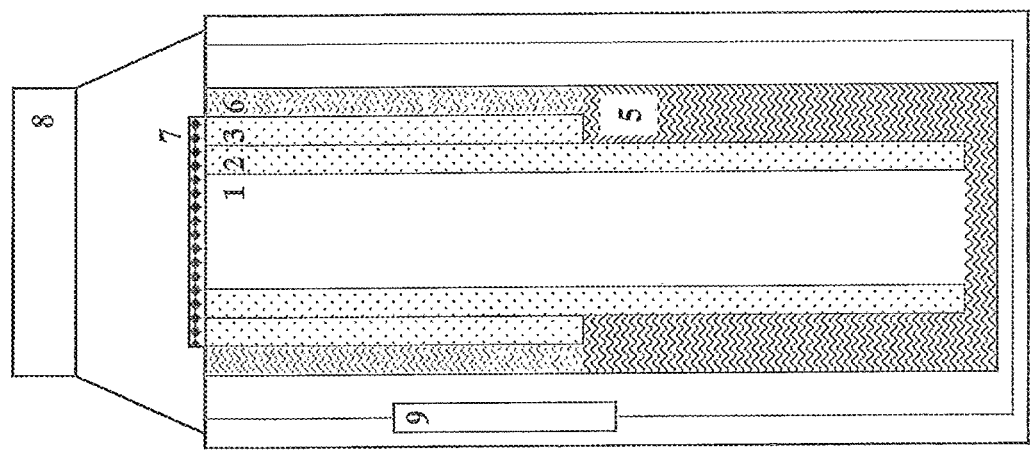
FIG. 2 is a schematic of an embodiment of an aerosol generator for generating an aerosol from two immiscible liquids that comprise two phases.

FIG. 2 is a schematic of an aerosol generator for generating an aerosol from two immiscible liquids that comprise two phases. A capillary tube 1 is concentrically surrounded by two layers 2, 3 of wicking materials, which transport liquids 5, 6, respectively, to the heating element 7. After the heating element 7 volatilizes the immiscible liquids to form volatilized fluid, the volatilized fluid may be transferred to a mouthpiece 8, from which formed aerosol may be inhaled. A control circuit 9 regulates the supply of power, preferably direct current, to the heating element 7. If desired, an additional phase may to be transported through the capillary tube 1.

Figure 3A:
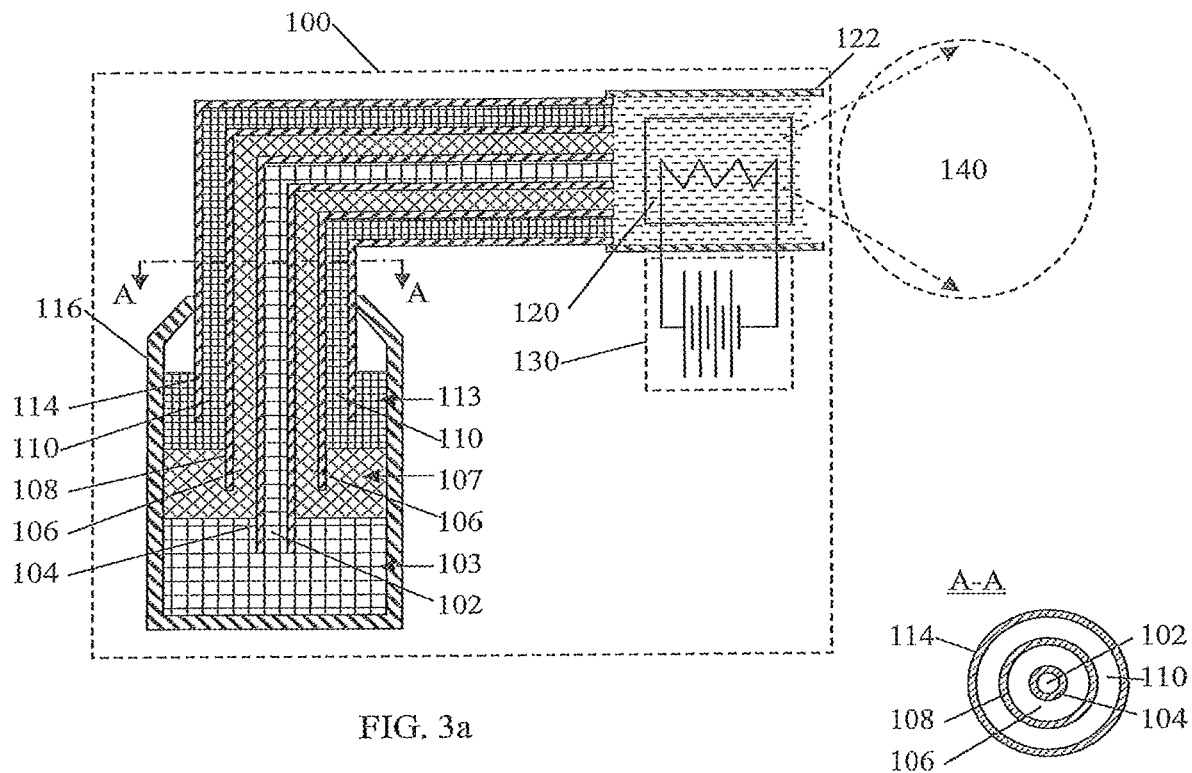
FIG. 3a shows a schematic of another embodiment of an aerosol generator having a composite conduit with multiple passages.

FIG. 3a is a schematic of another embodiment of an aerosol generator 100 for generating an aerosol from three immiscible liquids that comprise three phases. A reservoir 116 of the aerosol generator 100 is filled with the three liquids. A first capillary tube 104 is concentrically surrounded by second and third capillary tubes 108 and 114. First capillary tube 104 transports first liquid 103 which may be a hydrophilic liquid, to the heating element 120 from the reservoir 116. Second and third capillary tubes 108 and 114 transport second and third liquids 107 and 113, which may be neutral and hydrophobic liquids, respectively, to the heating element 120. After the heating element 120 volatilizes the immiscible liquids to form volatilized fluid, the volatilized fluid may be transferred to a mouthpiece 122, from which formed aerosol 140 may be inhaled. A control circuit 130 regulates the supply of power, preferably direct current, to the heating element 120.

Figure 3B:
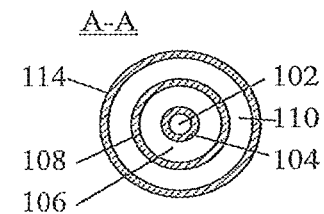

The concentric capillary tubes 104/108/114 form a composite conduit of the aerosol generator 100. FIG. 3b shows a cross section of the composite conduit of FIG. 3a at AA. As shown in FIG. 3b, when concentric capillary tubes are used, the distance between capillary sidewalls is comparable to the inner diameter of the center capillary tube as mentioned previously. For example, the distance between 104 and 108 or 108 and 110 in FIG. 3b. can be 0.1 to 10 mm, preferably 0.5 to 1 mm, more preferable about 0.1 to 0.5 mm, and even more preferably about 0.15 mm. Preferably, the capillary tube can be glass, porous metal, synthetic material and combinations thereof.

Figure 4:
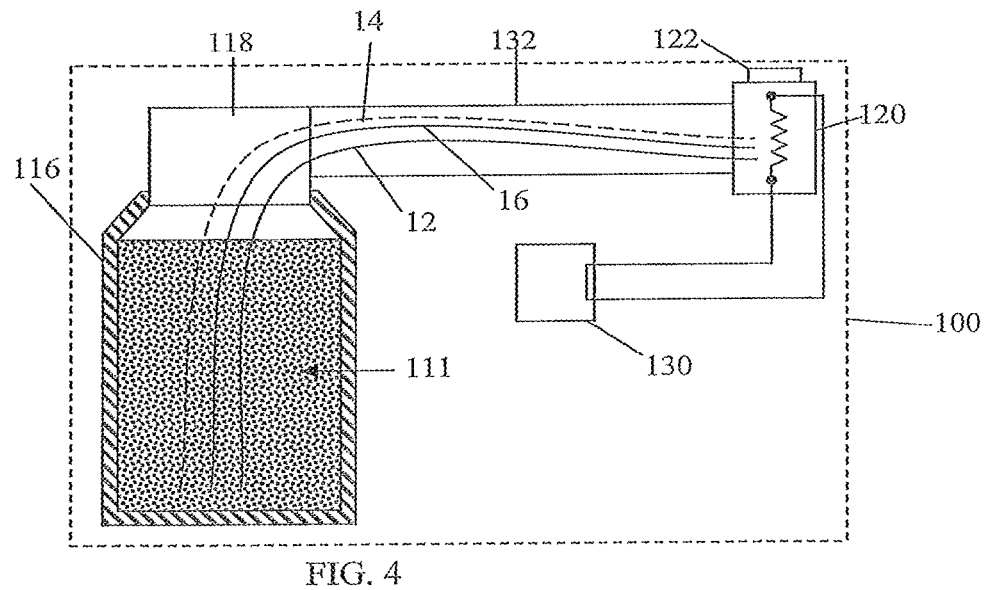
FIG. 4 shows a schematic of still another embodiment of an aerosol generator having a composite conduit with multiple passages.

FIG. 4 is a schematic of another embodiment of an aerosol generator 100 for generating an aerosol from three immiscible liquids that comprise three phases. A first wick 12 transports a first phase which may be a hydrophilic liquid, of a liquid 111 to the heating element 120 from a reservoir 116. In this embodiment, liquid 111 can be an emulsion of immiscible liquids (e.g., a hydrophilic liquid, a hydrophobic liquid and a neutral liquid or a combination of any two thereof). Second and third wicks 14 and 16 transport additional phases which may be neutral and hydrophobic liquids, respectively, of liquid 111 to the heating element 120. As shown in FIG. 4, the first, second and third wicks 12/14/16 may transport the liquids through a cap 118 of the reservoir 116 and through a passage 132 or the like, to the heating element 120. After the heating element 120 volatilizes the immiscible liquids to form volatilized fluid, the volatilized fluid may be transferred to a mouthpiece 122, as described previously. A control circuit 130 regulates the supply of power to the heating element 120, also as described previously.

In a preferred embodiment, first, second and third wicks 12/14/16 may be interwoven (e.g., braided) or separate. Interwoven wicks can be of various materials to transport the various phases. For example, synthetic wick materials to transport the hydrophilic phase can include plastic or rubber molecules with OH groups having an affinity for the polar phase liquids. Non-polar plastic material without OH group constituents have an affinity for the non-polar phase liquid and natural materials such as cotton have an affinity for the neutral phase liquid. As such, first second and third wicks 12/14/16 can transport separate phases from liquid 111 to the heating element 120 such that the phases are present at the heating element in desirable concentrations.

Also provided is a method of generating an aerosol comprising transporting immiscible liquids from at least one liquid supply to a heating element at rates such that the liquids are present at the heating element in desirable concentrations and volatilizing the immiscible liquids at the heating element to form volatilized fluid, which mixes with ambient air to form an aerosol with desirable concentrations of the immiscible liquids.

While various embodiments have been described, it is to be understood that variations and modifications may be resorted to as will be apparent to those skilled in the art. Such variations and modifications are to be considered within the purview and scope of the claims appended hereto.

What is claimed is:

1. A device for generation of an aerosol comprising:
   a reservoir containing a first liquid material and a second liquid material, the first liquid material having a first density, the second liquid material having a second density, and the first density being different from the second density such that the first liquid material and the second liquid material are in discrete, immiscible layers in the reservoir;
   a first wick in fluid communication with the reservoir;
   a second wick in fluid communication with the reservoir;
   at least one capillary tube surrounded by the second wick, the second wick surrounded by the first wick, the at least one capillary tube, the first wick, and the second wick having different lengths; and
   a heating element configured to heat the liquid material in the first wick and the second wick to form an aerosol, the heating element being a wire mesh on an end of the first wick or an end of the second wick.

2. The device of claim 1, wherein the heating element is formed of stainless steel.

3. The device of claim 1, further comprising:
   a power supply electrically connectable to the heating element.

4. The device of claim 3, wherein the power supply includes a battery.

5. The device of claim 3, further comprising:
   a control circuit configured to regulate a supply of power from the power supply to the heating element.

6. The device of claim 1, further comprising:
   a mouthpiece through which the aerosol passes.

7. The device of claim 1, wherein the first liquid material comprises an aerosol former and the second liquid material comprises a flavor system.

8. The device of claim 7, wherein the aerosol former comprises propylene glycol, glycerol, or both propylene glycol and glycerol.

9. The device of claim 1, wherein the first wick and the second wick are formed of different wicking materials.

10. The device of claim 1, wherein the capillary tube has an internal diameter between 0.1 mm and 10 mm.

11. The device of claim 10, wherein the capillary tube has an inner diameter between 0.1 mm and 0.5 mm.

12. The device of claim 1, wherein one of the first wick or the second wick includes a plastic or rubber material with —OH groups.

13. The device of claim 1, wherein one of the first wick or the second wick includes a non-polar plastic.

* * * * *